United States Patent [19]

Bordier et al.

[11] Patent Number: 5,686,085
[45] Date of Patent: Nov. 11, 1997

[54] LYSINE DERIVATIVES, PROCESS OF PREPARATION, USES, AND COMPOSITIONS COMPRISING THEM

[75] Inventors: Thierry Bordier, Tremblay; Michel Philippe, Wissous, both of France

[73] Assignee: L'Oreal, Paris, France

[21] Appl. No.: 590,444

[22] Filed: Jan. 23, 1996

[30] Foreign Application Priority Data

Jan. 31, 1995 [FR] France .................. 95 01113

[51] Int. Cl.⁶ .................. A61K 6/00; A61K 7/00
[52] U.S. Cl. .................. 424/401; 424/49; 424/54; 424/65; 424/69; 424/450; 426/534; 426/535; 426/289; 426/96; 426/98; 523/200; 523/207; 427/213.36; 427/215; 427/218; 427/220; 428/402; 428/402.22; 428/403; 106/414; 106/448; 106/465; 106/466; 106/469; 106/487; 106/489; 106/504; 106/505
[58] Field of Search .................. 562/556, 560; 424/401, 49, 54, 65, 69, 450; 426/534, 535, 289, 96, 98; 523/207, 200; 427/213.36, 215, 218, 220; 428/402, 402.22, 403; 106/414, 448, 465, 466, 469, 487, 489, 504, 505

[56] References Cited

U.S. PATENT DOCUMENTS

| 2,572,568 | 10/1951 | Gluesenkamp | 562/560 |
| 4,640,943 | 2/1987 | Meguro et al. | 523/200 |

FOREIGN PATENT DOCUMENTS

| A0139481 | 9/1984 | European Pat. Off. |
| A0336265 | 3/1989 | European Pat. Off. |
| A0447287 | 2/1991 | European Pat. Off. |

*Primary Examiner*—Frederick Krass
*Attorney, Agent, or Firm*—Finnegan, Henderson, Farabow, Garrett & Dunner, L.L.P.

[57] ABSTRACT

New lysine derivatives containing a containing an alkylsulphonyl or alkylaminocarbonyl group of formula (I):

$$COOH-CH(NH_2)-(CH_2)_4-NH-X$$

in which X represents an —SO₂R or —CONHR group, where R represents a linear or branched, saturated or unsaturated, alkyl radical having from 8 to 22 carbon atoms, salts thereof, and mixtures of the derivatives and the salts. A process for the preparation of these derivatives, salts, and mixtures and use of such derivatives, salts, and mixtures, especially in cosmetics. Compositions, especially cosmetic compositions, comprising the derivatives, salts, and mixtures.

38 Claims, No Drawings

LYSINE DERIVATIVES, PROCESS OF PREPARATION, USES, AND COMPOSITIONS COMPRISING THEM

The subject of the present invention is compounds containing an $N^\epsilon$-alkylsulphonyl or $N^\epsilon$-alkyl-aminocarbonyl group, which are derived from lysine, their process of preparation, their use, especially in cosmetics, and the compositions, especially cosmetic compositions, comprising them.

Compositions, especially cosmetic, pharmaceutical or food compositions, are known which can be provided in the form of a powder, known as a compact powder, obtained by compacting. They are generally anhydrous compositions which may be mainly composed of solid particles and of a fatty binder, shaped by compression.

The development of such compositions raises, however, many difficulties because the final composition must be sufficiently homogeneous and compact to have a good ability to be removed and, moreover, to avoid fragmentation which may be caused, especially, by impacts.

A description is given, in Patent Application EP 139,481, of cosmetic compositions using, as agents for modifying the surface of inorganic compounds, for the purpose of increasing the dispersibility thereof, either a monoacylated derivative of a basic amino acid in which the aliphatic acyl group has 8–22 carbon atoms or an N,N-diacylated derivative of a basic amino acid in which the acyl groups, which are identical or different, have 1–22 carbon atoms.

A description is also given, in Patent Application EP 336,265, of cosmetic compositions for hair shaping comprising, as surface-active agents, an N-monoacylated derivative of a basic amino acid in which the acyl group has 8–22 carbon atoms.

However, it is observed that the acylated derivatives of the basic amino acids described previously are very difficult and even impossible to compact.

The aim of the present invention is to provide new compounds which make it possible to facilitate the preparation of such compositions, while satisfying the abovementioned requirements, without exhibiting the disadvantages of the prior art.

The subject of the present invention is therefore a lysine derivative containing an $N^\epsilon$-alkyl-sulphonyl or $N^\epsilon$-alkylaminocarbonyl group of formula (I)

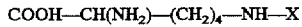

in which X represents an —$SO_2R$ or —CONHR group, where R represents a linear or branched, saturated or unsaturated, alkyl radical having from 8 to 22 carbon atoms, the salts of the compounds of formula (I), as well as their optical isomers of D or L configuration, and their mixtures.

Another subject of the invention is a composition, inter alia cosmetic, pharmaceutical, hygiene or food, comprising at least one derivative of formula (I).

A further subject of the invention is the use of at least one derivative of formula (I) as a substance for coating substrate particles. It has in fact been observed that the said particles, generally powders, had an improved feel when they were coated with the said derivative.

Moreover, it has been observed that the derivatives according to the invention also made it possible to confer particularly advantageous spreading, skin-adhesion and light-scattering qualities, as well as a pleasant and smooth feel and an improved water resistance, on the cosmetic composition comprising them.

More precisely, the subject of the invention is a lysine derivative of formula (I):

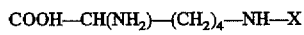

in which X represents an —$SO_2R$ or —CONHR group, where R represents a linear or branched, saturated or unsaturated, alkyl radical having from 8 to 22 carbon atoms, the salts of the compounds of formula (I), as well as their optical isomers of D or L configuration, and their mixtures.

The R radical can preferably represent a linear or branched alkyl radical preferably having 8 to 16 carbon atoms.

Mention may be made, amongst the derivatives according to the invention, of $N^\epsilon$-dodecylsulphonyl-L-lysine and $N^\epsilon$-dodecylaminocarbonyl-L-lysine.

The salts of the derivatives of formula (I) can be chosen from the salts of monovalent inorganic cations, such as those of sodium, or divalent inorganic cations, such as those of zinc or of copper. The salts can also be chosen from the salts of organic cations, such as those of aminopropanediol, trishydroxyaminomethane, glucamine and N-methylglucamine.

The derivatives according to the invention can be provided in a solid form having a particle size generally ranging from 10 to 500,000 nm and preferably ranging from 100 to 25,000 nm.

These derivatives generally have little solubility in oils and in aqueous solutions in which the pH ranges from 5 to 8. They generally have a high melting point, greater than 200° C.

The composition according to the invention comprising the said derivatives can be provided in various forms such as dispersions, optionally thickened or gelled lotions, optionally "compacted" powders, milks, creams, sticks, foams or sprays when it is packaged as an aerosol, oil-in-water or water-in-oil emulsions, liposomal dispersions or alternatively solid preparations.

The derivatives according to the invention can be included in the composition in a proportion generally ranging from 0.05% to 80% by weight, preferably in a proportion from 0.5 to 30% by weight, with respect to the total weight of the composition.

The derivatives according to the invention can be present in the composition in the free form and/or in the form of a combination with substrate particles which they coat.

In addition to the derivative according to the invention, the composition can also comprise at least one additive chosen from the group consisting of surface-active agents, fatty substances, organic solvents, silicones, thickeners, emollients, sunscreen agents, treating agents, anti-foaming agents, moisturizing agents, fragrances, preservatives, anti-oxidizing agents, sequestrants, flavouring agents, basifying or acidifying agents, fillers and pigments.

Mention may be made, among the fatty substances which can be used in the composition according to the invention, of oils, waxes, fatty acids, fatty alcohols and/or their mixture.

The oils and the waxes can be of animal, plant, inorganic or synthetic origin. Mention may be made, among the oils, of hydrogenated palm oil, hydrogenated castor oil, liquid petrolatum, liquid paraffin or purcellin oil.

Mention may be made, among the waxes, of beeswax, montan wax, carnauba wax, candelilla wax, sugar cane wax, Japan wax, ozocerite, microcrystalline waxes, paraffin wax, lanolin wax, hydrogenated lanolin wax and acetylated lanolin wax.

Mention may especially be made, among the particles which can be coated by the derivatives according to the invention, of pigments, particulate fillers and microspheres such as hollow vinylidene chloride/acrylonitrile copolymer microspheres. Mention may more particularly be made, among the fillers, of optionally coloured insoluble fillers such as nanopigments of metal oxides, such as titanium, zinc, iron, manganese, caesium and/or zirconium oxides.

The composition according to the invention can be provided in the form of make-up compositions such as foundation creams, tinted creams, mascaras, blushers, eye shadows, lipsticks or nail varnishes.

According to a specific embodiment, the composition according to the invention can be provided in the so-called compact form, the derivative according to the invention facilitating compaction of the ingredients of the said compositions and the cohesion of the compacted product, which prevents easy disintegration of the said compacted product.

Mention may especially be made, among these compact compositions, of foundation creams, blushers, eye shadows and lipsticks.

The composition according to the invention can also be provided in the form of a pharmaceutical or hygiene composition, such as toothpastes, exfoliative compositions, powders for the body or for babies, and anti-perspirant powders, or indeed in the form of a food composition.

Another subject of the invention is a process for the preparation of a derivative of formula (I), comprising the steps of:

reacting, in aqueous medium and at basic pH, lysine, at least one of its salts, or a mixture of lysine and at least one of its salts, of known configuration, with a copper salt solution;

reacting the solution of the copper complex with a compound of formula (II) chosen from:

R—SO$_2$—Cl  (IIa)

R—NH—CO—Y  (IIb), and

R—N=C=O  (IIc)

in which R represents a linear or branched, saturated or unsaturated, alkyl radical having from 8 to 22 carbon atoms and Y is chosen from the azole derivatives, such as the imidazolyl radical, the said compound of formula (II) being added with or without solvent, to form a copper salt;

treating the copper salt of the substituted lysine, salt, or mixture obtained with a decomplexing agent; and, optionally, purifying the lysine derivative, the salt, or the mixture obtained.

Mention may particularly be made, among the copper salt solutions used in the process according to the invention, of copper sulphate solutions.

The basic pH of the reaction medium preferably ranges from 8 to 14.

According to a preferred embodiment of the preparation process, the decomplexing agent used is an aqueous solution of the disodium salt of ethylenediaminetetraacetic acid or of an acid such as hydrochloric acid.

Examples of the preparation of lysine derivatives containing an N$^\epsilon$-alkylsulphonyl or N$^\epsilon$-alkyl-aminocarbonyl group according to the invention, and an example of a composition comprising such a derivative, will now be given by way of illustration only and do not limit the invention in any way.

EXAMPLE 1

Preparation of N$^\epsilon$-dodecylsulphonyl-L-lysine 10 g of L-lysine monohydrochloride are dissolved in 44 ml of a 10% aqueous sodium hydroxide solution in a 250 ml three-necked flask equipped with a thermometer and a 50 ml dropping funnel.

A solution of 6.8 g of copper sulphate pentahydrate in 40 ml of water is introduced into the reaction mixture.

4.6 g of sodium hydrogencarbonate are added to the homogeneous mixture, which has been cooled to a temperature of 5° C., followed by the dropwise addition of dodecanesulphonyl chloride in solution in THF.

After stirring overnight at room temperature, the reaction mixture is filtered and the precipitate, corresponding to the final product in the form of a copper complex, is washed with water and with acetone and then dried in an oven under reduced pressure. To remove the copper, the complex is treated at reflux for 4 hours with a 10% aqueous solution of the dehydrated disodium salt of ethylenediaminetetraacetic acid. The treatment can be repeated several times in order to obtain an entirely decomplexed product. 14 g (68% yield) of pearlescent white product are obtained.

Chemical analysis gives the following characteristics:

Melting: decomposition from 260° C. (measured on a Kofler stage)

Mass spectrum: m/z 379.2 (MH$^+$), 361.1, 335.2, 316.0

Elemental analysis: (C$_{18}$H$_{38}$N$_2$O$_4$S, molecular weight 378.579)

|  | C | H | N | O | S |
|---|---|---|---|---|---|
| % Calculated | 57.11 | 10.12 | 7.4 | 16.9 | 8.47 |
| % Measured | 56.84 | 10.05 | 7.28 | 16.98 | 8.72 |

Particle size (measured by light diffraction using a Leeds & Northrup Microtrac X 100 model): at 0.4% in an equimolar water/ethanol mixture, the following is obtained, by number (-average): 4.72 μm Thin layer chromatography: HPTLC (Merck 60F254 silica), with, as eluent, a 6/47/47 NH$_4$OH/CH$_3$OH/CH$_2$Cl$_2$ mixture.

The following frontal ratio is obtained: R$_f$=0.44.

EXAMPLE 2

Preparation of N$^\epsilon$-dodecylaminocarbonyl-L-lysine 10 g of L-lysine monohydrochloride are dissolved in 44 ml of a 10% aqueous sodium hydroxide solution in a 250 ml three-necked flask equipped with a thermometer and a 50 ml dropping funnel. A solution of 6.8 g of copper sulphate pentahydrate in 40 ml of water is introduced into the reaction mixture.

A solution of 15.3 g of N-(dodecylaminocarbonyl)-imidazole in 80 ml of THF is added at room temperature.

After stirring overnight at room temperature, the reaction mixture is filtered and the precipitate, corresponding to the final product in the form of a copper complex, is washed with water and with acetone and then dried in an oven under reduced pressure. To remove the copper, the complex is treated at reflux for 4 hours with a 10% aqueous solution of the dehydrated disodium salt of ethylenediaminetetraacetic acid. The treatment can be repeated several times in order to obtain an entirely decomplexed product. 31 g (79% yield) of a slightly bluish product are obtained.

Chemical analysis gives the following characteristics:

Melting: T>260° C. (Kofler stage)

Mass spectrum: m/z 358 (MH$^+$), 186

Elemental analysis ($C_{19}H_{39}N_3O_3$: molecular weight 357.541)

|  | C | H | N | O |
|---|---|---|---|---|
| % Calculated | 63.83 | 10.99 | 11.75 | 13.42 |
| % Measured | 63.67 | 11.02 | 11.37 | 13.32 |

Particle size (measured by light diffraction): at 0.4% in an equimolar water/ethanol mixture, the following is obtained by number (-average): 0.59 μm Thin layer chromatography: HPTLC (Merck 60F254 silica), eluent: 6/47/47 $NH_4OH/CH_3OH/CH_2Cl_2$ mixture.

The following frontal ratio is obtained: $R_f=0.36$.

EXAMPLE 3

A compacted powder is prepared which has the following composition:

| Composition A: | |
|---|---|
| Talc | 38.4 g |
| Bismuth oxychloride | 10 g |
| Zinc stearate | 4 g |
| Compound of Example 1 | 20 g |
| Nylon powder | 20 g |
| Composition B: | |
| Iron oxides | 1.6 g |
| Liquid petrolatum | 6 g |

The powder is obtained in the following way: the composition A is ground in a grinder of Kenwood type for approximately 5 minutes with slow agitation, the composition B is added and the entire mixture is ground for approximately 2 minutes at the same speed and then for 3 minutes at a faster speed. The preparation is then sieved on a 0.16 mm sieve and this mixture is then compacted into small dishes.

A compacted powder is obtained which has good adhesion and which spreads readily and pleasantly on the skin, while being smooth to the touch.

Moreover, the presence of the compound of Example 1 prevents excessively easy disintegration of the compacted product.

We claim:

1. At least one lysine derivative having the formula:

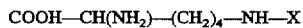

COOH—CH(NH$_2$)—(CH$_2$)$_4$—NH—X wherein X represents an —SO$_2$R or CONHR group in which R represents a linear or branched, saturated or unsaturated, alkyl radical having from 8 to 22 carbon atoms, at least one salt of said lysine derivative or a mixture of said least one lysine derivative and said at least one salt of said lysine derivative.

2. At least one derivative or at least one salt according to claim 1, wherein said derivative or said salt is an optical isomer of D or L configuration.

3. At least one salt according to claim 1 wherein said salt is a salt of a monovalent inorganic cation, a divalent inorganic cation, or an organic cation.

4. At least one salt according to claim 3 wherein said monovalent inorganic cation is sodium.

5. At least one salt according to claim 3 wherein said divalent inorganic cation is zinc or copper.

6. At least one salt according to claim 3 wherein said organic cation is a cation of aminopropanediol, trishydroxyaminomethane, glucamine, or N-methylglucamine.

7. At least one derivative according to claim 1 wherein said derivative is N$^\epsilon$-dodecylsulphonyl-L-lysine or N$^\epsilon$-dodecylamino-carbonyl-L-lysine.

8. At least one derivative or at least one salt according to claim 1 wherein said R radical represents a linear or branched alkyl radical having from 8 to 16 carbon atoms.

9. At least one derivative or at least one salt according to claim 1 wherein said derivative or said salt has a particle size ranging from 10 nm to 500,000 nm.

10. At least one derivative or at least one salt according to claim 9 wherein said particle size ranges from 100 nm to 25,000 nm.

11. A composition comprising as one of its components, at least one lysine derivative according to claim 1, at least one salt of said derivative, or a mixture of said at least one derivative and said at least one salt.

12. A composition according to claim 11, said composition being a dispersion, an optionally thickened or gelled lotion, an optionally compacted powder, a milk, a cream, a stick, a foam, a spray, an oil-in-water emulsion, a water-in-oil emulsion, or a liposomal dispersion.

13. A composition according to claim 11 wherein said derivative, said salt, or said mixture ranges from 0.05% to 80% by weight with respect to the total weight of the composition.

14. A composition according to claim 13 wherein said derivative, said salt, or said mixture ranges from 0.5% to 30% by weight with respect to the total weight of the composition.

15. A composition according to claim 11 wherein said derivative, said salt, or said mixture is in the free form, is in the form of a combination with substrate particles coated by said derivative, said salt, or said mixture, or is in the form of a mixture of said free form and said combination.

16. A composition according to claim 15 wherein said substrate particles are selected from pigments, particulate fillers or microspheres.

17. A composition according to claim 16 wherein said microspheres are hollow vinylidene chloride/acrylonitrile copolymer microspheres.

18. A composition according to claim 11 further comprising at least one additive selected from surface-active agents, fatty substances, organic solvents, silicones, thickeners, emollients, sunscreen agents, treating agents, anti-foaming agents, moisturizing agents, fragrances, preservatives, anti-oxidizing agents, sequestrants, flavouring agents, basifying or acidifying agents, fillers, or pigments.

19. A composition according to claim 18 wherein said fatty substances are selected from oils, waxes, fatty acids, or fatty alcohols.

20. A composition according to claim 19 wherein said oils are of animal, vegetable, inorganic, or synthetic origin.

21. A composition according to claim 20 wherein said oil is hydrogenated palm oil, hydrogenated castor oil, liquid petrolatum, liquid paraffin or purcellin oil.

22. A composition according to claim 19 wherein said waxes are of animal, vegetable, inorganic or synthetic origin.

23. A composition according to claim 22 wherein said wax is beeswax, montan wax, carnauba wax, candelilla wax, sugar cane wax, Japan wax, ozocerite, microcrystalline waxes, paraffin wax, lanolin wax, hydrogenated lanolin wax or acetylated lanolin wax.

24. A composition according to claim 16 wherein said particulate fillers are optionally coloured insoluble fillers.

25. A composition according to claim 24 wherein said optionally coloured insoluble fillers are nanopigments of metal oxides.

26. A composition according to claim 25 wherein said nanopigments of metal oxides are selected from titanium, zinc, iron, manganese, caesium or zirconium oxides.

27. A composition according to claim 11 wherein said composition is in the form of a make-up composition.

28. A composition according to claim 27, said make-up composition being a foundation cream, a tinted cream, a mascara, a blusher, an eye shadow, a lipstick or a nail varnish.

29. A composition according to claim 27, said make-up composition being in the compact form.

30. A composition according to claim 29, said make-up composition being a foundation cream, a blusher, an eye shadow or a lipstick.

31. A composition according to claim 11, said composition being a cosmetic composition, a pharmaceutical composition, a hygiene composition, or a food composition.

32. A composition according to claim 31, said composition being a toothpaste, an exfoliative composition, a skin-care composition, a body powder, or an anti-perspirant.

33. A process for the preparation of a derivative, salt, or mixture according to claim 1 comprising the steps of:

reacting lysine, at least one salt of lysine or a mixture of lysine and at least one of said salts in an aqueous medium and at a basic pH, with a copper salt solution to form a copper complex solution;

reacting said solution of the copper complex with a compound of formula (II) chosen from:

$$R-SO_2-Cl \quad \text{(IIa)};$$

$$R-NH-CO-Y \quad \text{(IIb)};$$

or $$R-N=C=O \quad \text{(IIc)}$$

wherein R represents a linear or branched, saturated or unsaturated, alkyl radical having from 8 to 22 carbon atoms and Y represents an azole derivative, to obtain a copper salt;

treating said copper salt with a decomplexing agent to obtain said derivative, said salt or said mixture; and optionally purifying said derivative, said salt or said mixture.

34. A process according to claim 33 wherein said azole derivative is an imidazolyl radical.

35. A process according to claim 33 wherein said copper salt solution is a copper sulphate solution.

36. A process according to claim 33 wherein said decomplexing agent is an aqueous solution of the disodium salt of ethylenediaminetetra-acetic acid or of hydrochloric acid.

37. A method of coating a substrate particle comprising the step of coating a substrate particle with said derivative, said salt, or said mixture according to claim 1.

38. A method for facilitating compaction of compositions including particles comprising the steps of including in a composition at least one derivative, at least one salt, or a mixture according to claim 1, either as particles or as a coating on substrate particles, said coated substrate particles being included in said composition; and thereafter compacting said composition.

* * * * *